(12) United States Patent
Meyer et al.

(10) Patent No.: US 12,268,823 B1
(45) Date of Patent: Apr. 8, 2025

(54) MAKING A SINGLE-USE RADIO-FREQUENCY ABLATION CATHETER REUSABLE

(71) Applicants: Chris Meyer, Windermere, FL (US); Seth Masek, Dover, FL (US)

(72) Inventors: Chris Meyer, Windermere, FL (US); Seth Masek, Dover, FL (US)

(*) Notice: Subject to any disclaimer, the term of this patent is extended or adjusted under 35 U.S.C. 154(b) by 0 days.

(21) Appl. No.: 18/742,125

(22) Filed: Jun. 13, 2024

(51) Int. Cl.
*A61M 25/00* (2006.01)
*A61B 18/14* (2006.01)
*A61B 18/00* (2006.01)

(52) U.S. Cl.
CPC ..... *A61M 25/0009* (2013.01); *A61B 18/1492* (2013.01); *A61B 2018/00577* (2013.01); *A61M 2025/0019* (2013.01); *A61M 2205/70* (2013.01)

(58) Field of Classification Search
CPC ...... A61M 25/0009; A61M 2025/0019; A61M 2205/70; A61B 18/1492; A61B 2018/00577
See application file for complete search history.

(56) References Cited

U.S. PATENT DOCUMENTS

| | | | |
|---|---|---|---|
| 2021/0023348 A1* | 1/2021 | Matsushita | G06Q 50/22 |
| 2022/0080469 A1* | 3/2022 | Sundet | B08B 9/043 |

* cited by examiner

*Primary Examiner* — Lee A Holly
(74) *Attorney, Agent, or Firm* — Robert Brownstein

(57) ABSTRACT

The invention is a method for restoring the use of a single-use RFA catheter system wherein the catheter is restored to first-use clean and sterilized status, and operating restrictions have been circumvented without affecting the first-use operational specifications.

2 Claims, 5 Drawing Sheets

MAKING A SINGLE-USE RADIO-FREQUENCY ABLATION CATHETER REUSABLE

TECHNICAL FIELD

The invention is a method for reusing a single-use radio-frequency catheter.

BACKGROUND OF INVENTION

Endovenous radiofrequency ablation is a minimally invasive treatment for varicose veins and venous insufficiency. The underlying cause of varicose veins is often the backward flow of blood in the Greater Saphenous Vein, Short Saphenous Vein, or Accessory Saphenous Vein. This backward flow of blood leads to dilation and venous hypertension of the venous tributaries associated with the Saphenous Veins. This dilation and venous hypertension manifests as varicose veins, chronic edema, venous stasis dermatitis and venous stasis ulcer. Endovenous Radiofrequency Ablation treats venous insufficiency by closing the refluxing saphenous veins. During the procedure, a catheter is inserted into the vein under ultrasonic guidance. It is then positioned in the proximal portion of the vein, making sure that it is a safe distance from the deep venous system, using ultrasound guidance. Once the catheter is properly positioned, tumescent anesthesia consisting of a local anesthetic and saline solution is injected into the tissue surrounding the vein. The radiofrequency ablation catheter is then connected to a computer-controlled radiofrequency generator. When the generator is activated, radiofrequency energy is delivered to the catheter and emitted from the heating element on the distal portion of the catheter. Once the target temperature is achieved, a negative feedback loop is used to maintain that temperature without causing excessive heat. The radiofrequency energy causes the collagen in the vein wall to shrink, the vein wall to collapse, and the vein to seal shut. Activation of the generator delivers timed (i.e. 20 second) cycles of energy to the catheter tip. The catheter is sequentially withdrawn along the length of the vein in a segmental pull-back protocol. Multiple segments are treated with overlap. At the completion of the procedure, the RF catheter is removed from the vein and pressure is held.

Some manufacturers of RFA catheters include use restrictions in their products. These may restrict how long the catheter may be operational and restrict its use to a single-use operation.

Because the RF generator and RFA catheter are separate components, the RF generator may be reused unconditionally but a new, costly, RFA catheter may be required each time a procedure is done.

There are methods for restoring the safety of a previously used RFA catheter by ensuring its physical and operational integrity, and by effectively cleaning and sterilizing the catheter to equivalent first-use status.

However, where an RFA catheter is intentionally restricted to single-use operation, despite being processed to equivalent first-use status, it will be unusable.

BRIEF DESCRIPTION OF INVENTION

The invention is a method for both restoring the RFA catheter to first-use status and circumventing certain use restrictions that prevent its reuse. In the case of one of the most used RFA catheters, with single-use restriction circuitry, the method comprises standard practices for cleaning and sterilizing plus a method for circumventing single-use restriction. The same method could be used for other RFA catheters that employ use restrictions affecting control electronics in the catheter's control-and-manipulation handle.

DETAILED DESCRIPTION OF INVENTION

In the United States, it has been well documented that health costs are significantly higher than in other first-world countries whereas any benefit of that increased cost cannot be quantified.

It is well known that the same pharmaceutical can be purchased in Canada, for example, at a significantly lower price than in the United States.

The US government has made the cost of healthcare a target for action, and has set a cap, for example, on the price of insulin for a category of users. One area that is not well publicized is where manufacturers have imposed use restrictions on reuse of costly instruments where, arguably, there is no valid reason for the use restriction other than its impact on demand and sales.

The use of RF ablation procedures as a means of treating venous insufficiency is well known. The devices used for such procedures involve catheters that are inserted into the diseased vein where they can heat the vein wall causing collagen shrinking and thrombosis of the vein.

Figure 1:
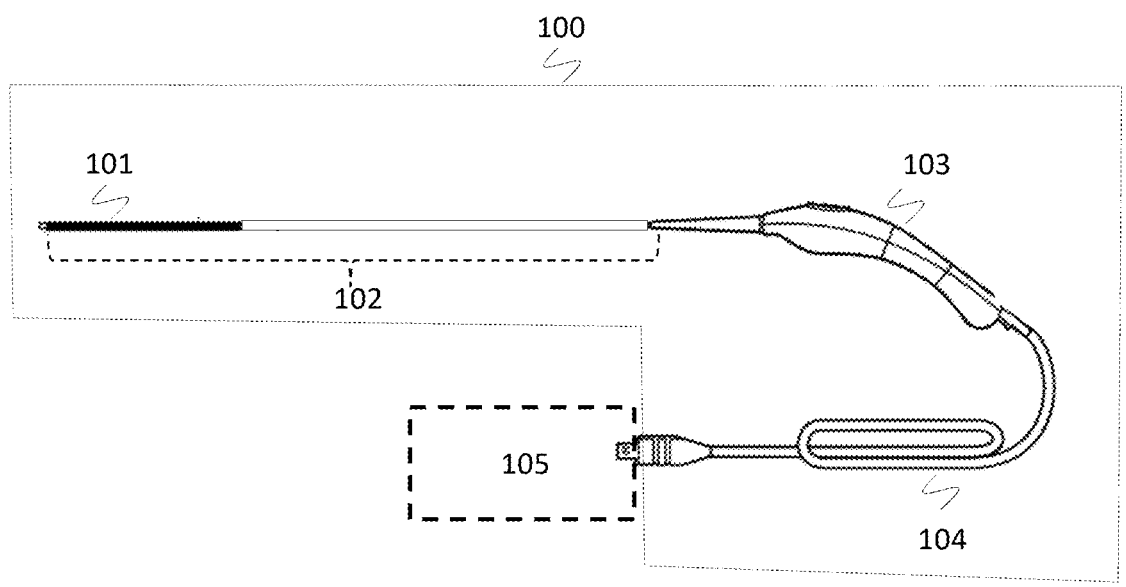
FIG. 1 shows an exemplary RFA catheter system.

As shown in FIG. 1, an RFA catheter system comprises the catheter portion (100) which comprises an insertion structure (101 and 102), a manipulation and control handle (103), a cable (104) for conveying RF energy to the 101 structure via interface to the RF generator (105). Because the subsystems (RF generator and catheter) are separable, the RF generator can be reused without restriction. However, use restrictions that limit catheter use to a single operation require that the costly catheter portion be replaced after a single use.

Figure 2:
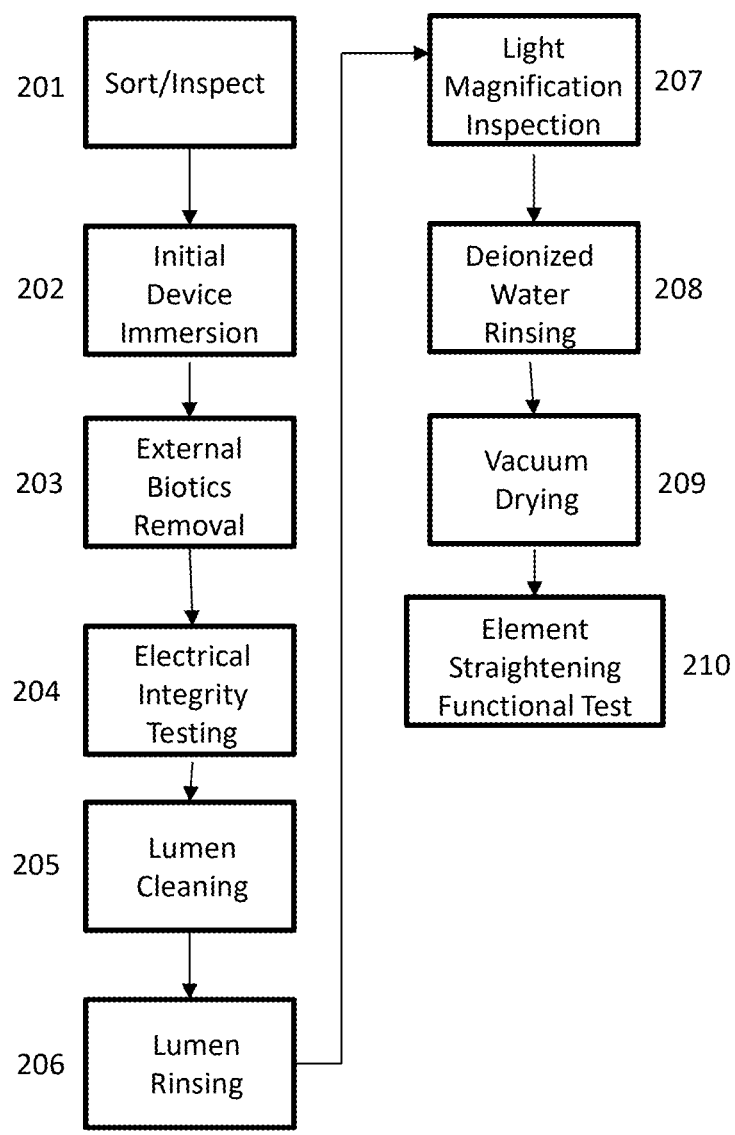
FIG. 2 is a flow diagram for cleaning and sterilizing a previously used RFA catheter.

FIG. 2 shows an accepted method for restoring a previously used RFA catheter to first-use clean-and-sterilized status. It begins with sorting and visually inspecting a previously used catheter (201) wherein visibly damaged devices are safely discarded and visibly undamaged ones proceed to an immersion step (202) in which all biotic substances and other soiling particulates are immersed in a protease enzyme solution that effectively removes them from catheter surfaces and interiors. This is followed by a subsequent inspection and removal of any external biotic substances that remain (203). The next process step is placing the catheter into an electrically conducting liquid (low resistance) wherein the insulating integrity of the catheter is now checked. When resistance between probe and shaft reads low resistance, that indicates insulation failure, and the device is safely discarded. Next (204) all catheter lumens (tubes) are cleaned and rinsed (205 and 206). Then, (207) the catheter undergoes a lighted, magnified inspection for any remaining substances. Afterward, the catheter is rinsed (208) in deionized water, then vacuum dried (209) and its insertion elements straightened (210). At this point, the catheter is in first-use clean status and a subsequent sterilization step achieves full first-use status.

If, however, the catheter has an imposed use restriction built into its system, the catheter in first-use clean and sterilized condition is effectively unusable. Any use-restriction structures and functions must be identified and circumvented. In so doing, it is crucial that once circumvented, and operational, the processed catheter meets all first-use operational specifications.

Figure 3:
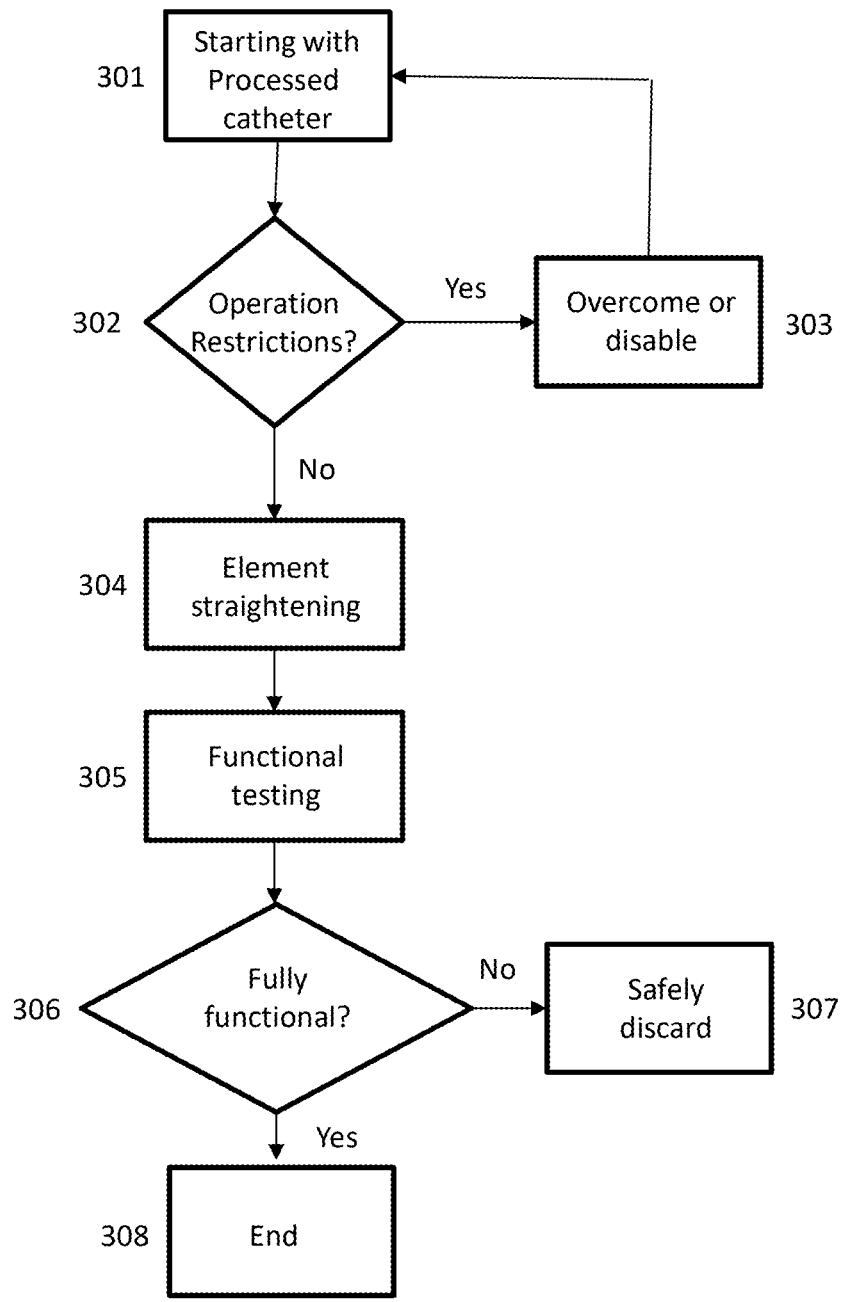
FIG. 3 is a flow diagram for determining and circumventing use restrictions in an RFA catheter.

In FIG. 3, a segment of new method steps are inserted between steps 209 and 210 of FIG. 2. Here, starting with the processed catheter at step 209 in FIGS. 2 and 301 in FIG. 3, in step 302 any use restrictions must be identified. If possible, these restrictions are then circumvented (303), and only then is element straightening (304), functional testing (305, 306 and 307) done. At the end (308) one now has a previously used RFA catheter that attains first-use clean and sterilized status, and is operational (without use restrictions) while meeting or exceeding all original-equipment, first-use operational specifications.

Figure 4:
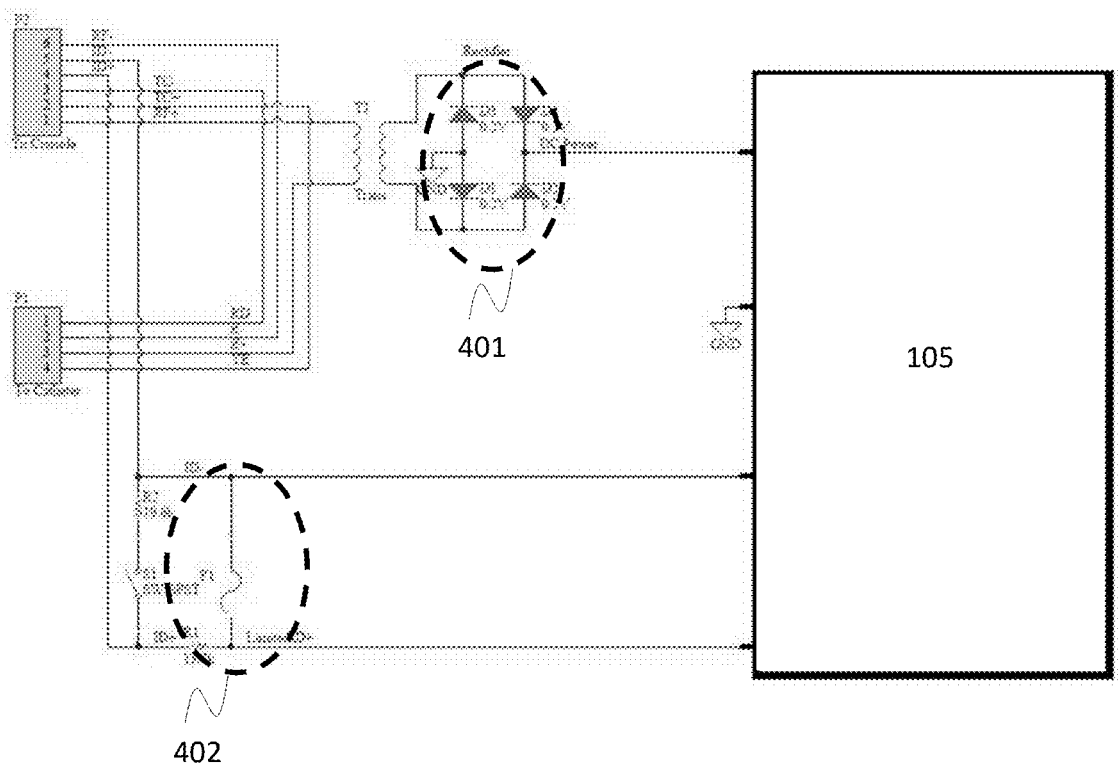
FIG. 4 is an example of a use-restriction circuit prior to circumvention.

To illustrate how use restrictions may be circumvented without affecting first-use operational specifications, the FIG. 4 shows an actual RFA catheter schematic having a single-use restriction. After a single use, the circuitry is designed such that fuse, F1, will blow disrupting the connection between the catheter and the RF generator (101). The three circuit elements that enable that single-use restriction are the four diodes shown as 401, circuitry in box 105, and the fuse, F1, shown as 402.

Figure 5:
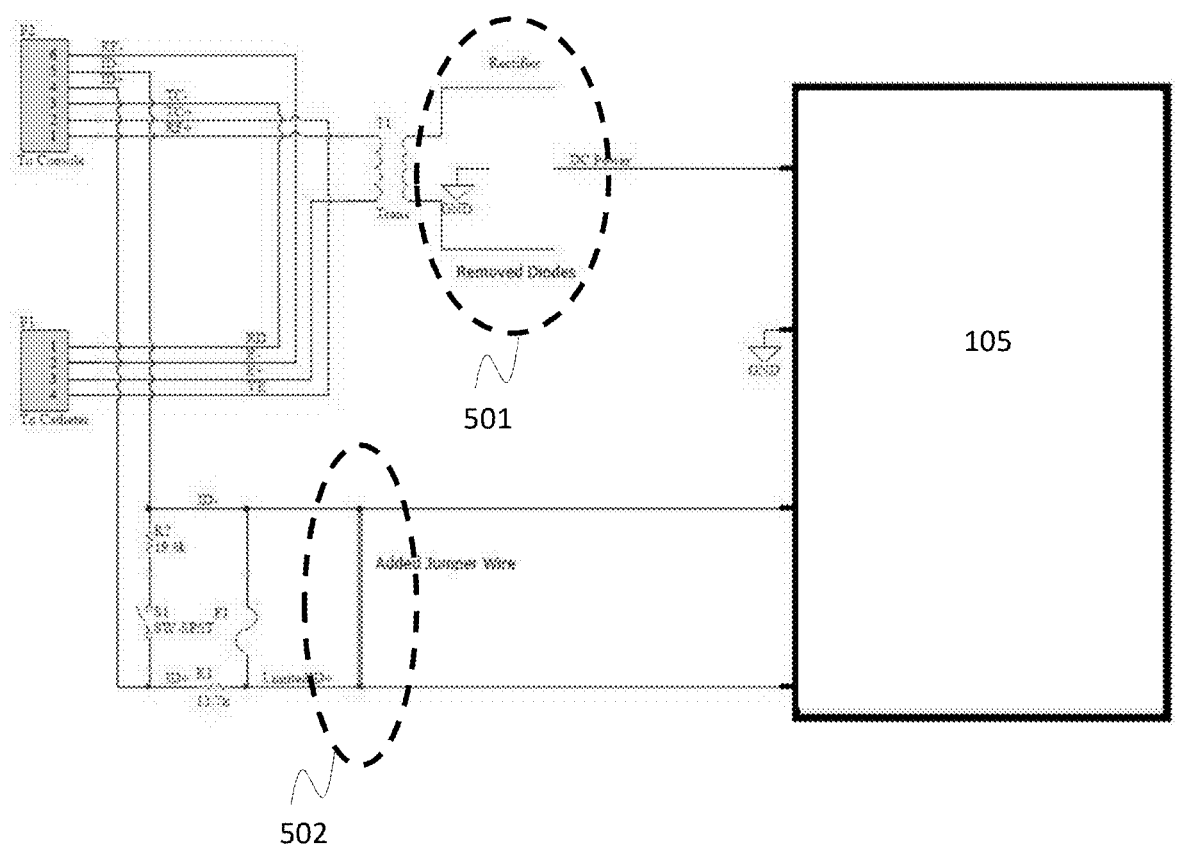
FIG. 5 is an example of a use-restriction circuit that has been circumvented.

FIG. 5 shows the circumvention step wherein the diodes are removed from the circuitry (501) and the fuse, F1, is paralleled by a jumper wire (502). Removing the diodes removes power to circuitry in box 105 to prevent an attempt to short the installed jumper wire. Once circumvented, the catheter may be reused, processed to first-use clean/sterilization status, and reused, again.

In the exemplary case (FIGS. 4 and 5), the circuitry is contained within the manipulation and control handle (FIG. 1, 103) which must be carefully opened to gain access to the printed-circuit board allowing diode removal and/or fuse being jumped.

The steps in the process of FIG. 2 are in a prescribed order. The steps for the process of FIG. 3 can be done after 209 of FIG. 2, or before the process of FIG. 2. Since it is most likely to involve the manipulation and control handle, it should not affect the clean/sterilized status of the inserted portion of the catheter, so its position in the flow is not critical.

What is claimed is:

1. A method for safely restoring use of a previously used RFA catheter comprising:
    inspecting, visually, a previously used RFA catheter for visible damage;
        if visibly damaged, then safely discarding the previously used RFA catheter;
        otherwise if visibly undamaged, then,
    immersing the previously used RFA catheter in a protease enzyme solution;
    removing, manually, after immersing, any remaining biotic substances;
    checking for insulation failure between probe and shaft of the previously used RFA catheter;
        if low resistance is measured between probe and shaft, then safely discarding the previously used RFA catheter;
        otherwise flushing the previously used RFA catheter's lumen with NaOCl;
    rinsing, after flushing the catheter's lumen, with deionized water;
        inspecting, using light and magnification, the previously used RFA catheter, now flushed and rinsed, for any remaining biotic substances;
            if any biotic substances remain, then safely discarding the previously used RFA catheter;
            otherwise rinsing the entire catheter in deionized water;
        vacuum drying the now rinsed previously used RFA catheter;
    determining if the vacuum-dried catheter has any operational restrictions, and then
    circumventing the restrictions by physically modifying the hardware.

2. A method claim as in claim 1 further comprising:
    executing a test of all functions of the previously used RFA catheter, which has had any operating restrictions circumvented;
        if the previously used RFA catheter is fully functional and operating as specified, then end the restoration process;
        if the previously used RFA catheter is not fully functional and is not operating as specified, then discard safely.

\* \* \* \* \*